US00PP31522P2

(12) United States Plant Patent
Pierron-Darbonne

(10) Patent No.: US PP31,522 P2
(45) Date of Patent: Mar. 10, 2020

(54) BLUEBERRY PLANT NAMED 'PLABLUE 15122'

(50) Latin Name: ***Vaccinium corymbosum* L.**
Varietal Denomination: Plablue 15122

(71) Applicant: Plantas de Navarra, S.A. Sociedad Unipersonal, Navarra (ES)

(72) Inventor: Alexandre Pierron-Darbonne, Pamplona (ES)

(73) Assignee: Plantas de Navarra, S.A. Sociedad Unipersonal, Valtierra, Navarra (ES)

( * ) Notice: Subject to any disclaimer, the term of this patent is extended or adjusted under 35 U.S.C. 154(b) by 0 days.

(21) Appl. No.: 16/501,255

(22) Filed: Mar. 13, 2019

(51) Int. Cl.
*A01H 5/08* (2018.01)
*A01H 6/36* (2018.01)

(52) U.S. Cl.
USPC ..... Plt./157
CPC ..... *A01H 6/36* (2018.05)

(58) Field of Classification Search
USPC ..... Plt./157
CPC ..... A01H 5/08
See application file for complete search history.

*Primary Examiner* — Kent L Bell
(74) *Attorney, Agent, or Firm* — Knobbe, Martens, Olson & Bear, LLP

(57) ABSTRACT

Descried herein is a new and distinct blueberry variety with varietal denomination 'Plablue 15122', characterized by a combination of traits which include, a semi upright plant growth habit, and very abundant production of medium fruit-size, round shaped and very firm fruit. 'Plablue 15122' is a self-fertile variety.

17 Drawing Sheets

Botanical classification: *Vaccinium corymbosum* L.

Variety denomination: The new plant has the varietal denomination 'Plablue 15122'.

CROSS-REFERENCE TO RELATED APPLICATIONS

This application claims the benefit of European Community Plant Variety Office Application No. 2018/2076, for a blueberry variety named 'Plablue 15122', filed on Aug. 9, 2018, the entirety of which is incorporated by reference herein.

BACKGROUND

Disclosed herein is a new and distinct southern highbush blueberry variety (*Vaccinium corymbosum* L.). The varietal denomination of the new variety is 'Plablue 15122'. The new variety of blueberry was created in a breeding program by crossing two parents; in particular, by crossing as seed parent an undistributed blueberry parent designated 14.09.001 (unpatented) and as pollen parent an undistributed blueberry parent designated 11.024.001 (unpatented). Female and male are selections from breeder's program. Both parental varieties are property and have not been commercialized.

The new variety was grown and asexually propagated by softwood cuttings in Segovia, Spain, 3° 59'W., 41° 22'N., 2742 feet elevation. Clones of the new variety were further asexually propagated and extensively tested. This propagation and testing has demonstrated that the combination of traits disclosed herein which characterize the new variety are fixed and retained true to type through successive generations of asexual reproduction.

The growing period in Huelva, Spain, where the observations on primocane production were made, is between about November 20 and June 22 of the following year.

SUMMARY

The present invention relates to a new and distinct southern highbush blueberry variety. The varietal denomination of the new variety is 'Plablue 15122', that produces and maintains a medium vigorous plant with consistent fruit production from the end of January through the end of May. Among the characteristics which appear to distinguish the new variety from other varieties are a combination of traits which include a semi upright plant growth habit, and very abundant production of medium fruit-size, round shaped and very firm fruit.

The new blueberry plant variety 'Plablue 15122' has not been observed under all possible environmental conditions. The phenotype may vary somewhat with variations in environmental and cultural practices such as temperature and light intensity without, however, any variance in genotype.

COMPARISON TO THE PARENTS

The seed and pollen parents were both obtained by Plantas de Navarra, S.A. Sociedad Unipersonal. They are selections from the breeder's program of Plantas de Navarra, S.A. Sociedad Unipersonal. They are property of Plantas de Navarra, S.A. Sociedad Unipersonal. Plantas de Navarra, S.A. Sociedad Unipersonal maintains them in their nurseries.

The new variety is distinguished from its parents by the following characteristics possessed by 'Plablue 15122' which are different than, or not possessed, by the seed parent designated '14.09.001' (unpatented) and the pollen parent designated '11.024.001' (unpatented).

Length of leaf of seed parent '14.09.001' (unpatented) is longer than length of leaf of 'Plablue 15122'.

Length of the internode on the one-year-old shoot of the seed parent '14.09.001' (unpatented) is longer than the length of the internode on the one-year-old shoot of 'Plablue 15122'.

Shape of the corolla of the flower of seed parent '14.09.001' (unpatented) is urceolate to cyllindrical, whereas the shape of the corolla of the flower of 'Plablue 15122' is urceolate.

Shape of corolla of flower of pollen parent '11.024.001' (unpatented) is urceolate to cyllindrical, whereas shape of corolla of flower of 'Plablue 15122' is urceolate.

Leaf of the pollen parent '11.024.001' (unpatented) shows a margin entire, whereas the leaf of 'Plablue 15122' shows a margin serrate.

Length of the internode on the one-year-old shoot of pollen parent '11.024.001' (unpatented) is longer than the length of the internode on the one-year-old shoot of 'Plablue 15122'.

COMPARISON TO CLOSEST VARIETY

The new variety is closest to the variety 'Biloxi' (unpatented), but is distinguished therefrom by the following characteristics possessed by 'Plablue 15122' which are different than, or not possessed by 'Biloxi'.

Plant of 'Biloxi' (unpatented) exhibits a weak vigor, whereas the plant of 'Plablue 15122' exhibits a medium vigor.

Length of inflorescence of 'Biloxi' (unpatented) is shorter than the length of inflorescence of 'Plablue 15122'.

Anthocyanin coloration of the flower bud of 'Biloxi' (unpatented) is weak, whereas anthocyanin coloration of the flower bud of 'Plablue 15122' is strong.

Density of fruit cluster of 'Biloxi' is higher than the density of fruit cluster of 'Plablue 15122'.

Fruit shape of 'Biloxi' (unpatented) is oblate, whereas in 'Plablue 15122' fruit shape is round.

Depth of the calyx basin in the fruit of 'Biloxi' (unpatented) is shallow, whereas depth of the calyx in the fruit of 'Plablue 15122' is medium depth.

Fruit of 'Biloxi' (unpatented) shows a soft firmness, whereas fruit of 'Plablue 15122' shows a very firm firmness.

Time of beginning of flowering on the one-year-old shoot of 'Biloxi' (unpatented) is less early than in 'Plablue 15122'.

Time of beginning of fruit ripening on the one-year-old shoot of 'Biloxi' (unpatented) is less early than in 'Plablue 15122'.

Differences in vigor of 'Plablue 15122' (designated 15.06.109) and 'Biloxi' (unpatented) are shown in FIG. 1 and FIG. 13. Differences in length of inflorescence of 'Plablue 15122' (designated 15.06.109) and 'Biloxi' (unpatented) is shown in FIG. 3 and FIG. 14. Differences in anthocyanin coloration of flower bud 'Plablue 15122' (designated 15.06.109) and 'Biloxi' (unpatented) are shown in FIG. 3 and FIG. 14. Differences in density of fruit cluster of 'Plablue 15122' (designated 15.06.109) and 'Biloxi' (unpatented) are shown in FIG. 8 and FIG. 15. Differences in fruit shape of 'Plablue 15122' (designated 15.06.109) and 'Biloxi' (unpatented) are shown in FIG. 9 and FIG. 16. Differences in depth of calyx basin in the fruit of 'Plablue 15122' (designated 15.06.109) and fruit of 'Biloxi' (unpatented) are shown in FIG. 9, FIG. 11, FIG. 16, and FIG. 17. These differences are maintained during the harvest season.

BRIEF DESCRIPTION OF THE ILLUSTRATIONS

The accompanying photographs show typical specimens of the new variety, designated 15.06.109 in the illustrations, including fruit, foliage and flower, in color as nearly true as it is reasonably possible to make in color illustrations of this character.

The plants depicted in the drawings were planted October 14 in the farm in Cartaya (Huelva), Spain, about 7° W, 37° N, 45 feet elevation.

Drawings/photographs were taken in April (about April 4 and April 12): minimum temperate about 7° to 9° Centigrade, maximum temperate about 18 to 22° Centigrade.

FIG. 1 and FIG. 2 show several plants of the new variety (designated 15.06.109) which exhibit a semi upright habit plant with several clusters of violet-blue color fruit (RHS Violet-Blue group color near 97 C to 97 B) with wax and rounded shape fruits.

FIG. 3 and FIG. 4 show the upper side and the underside, respectively, of a complete leave of the new variety (designated 15.06.109). In it, we can see that the leaf color of upper side of the leaf of the new variety (designated 15.06.109) is a yellow-green color (RHS Yellow-Green group color near 147 B to 147 A) and the leaf color of the underside of the leaf of the new variety (designated 15.06.109) is a yellow-green color (RHS Yellow-Green group color near 148 D to 148 C).

FIG. 5 shows clusters with immature flowers of the new variety (designated 15.06.109). In it, we can see the Immature flower red color (RHS Red group color near 55 D to 55 B).

FIG. 6 shows a typical flower of the new variety (designated 15.06.109). In it, we can see the corolla of the new variety (designated 15.06.109) with white color (RHS White group color near 155 B to 155 A).

DESCRIPTION OF THE NEW VARIETY

Figure 1:
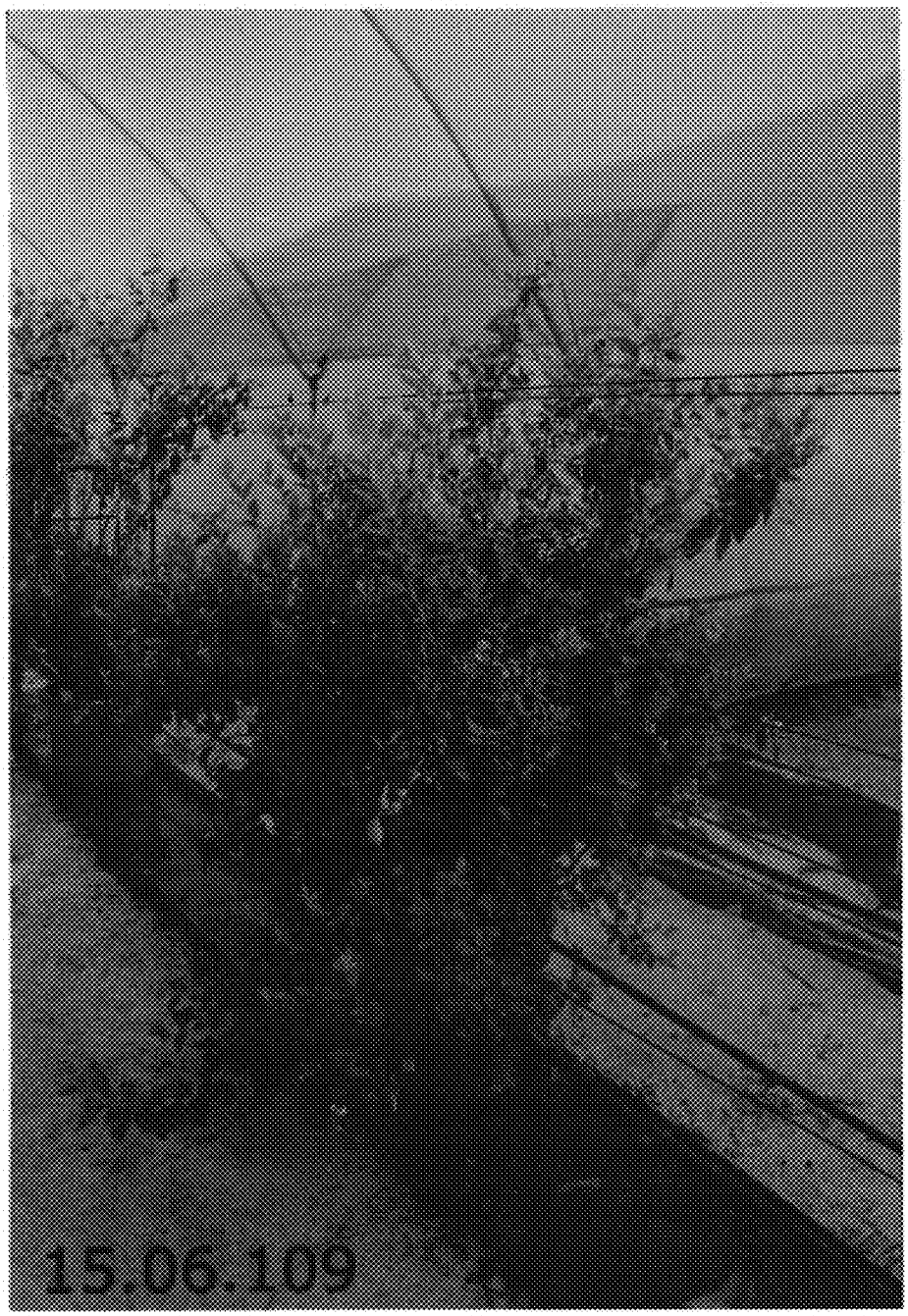
Figure 2:
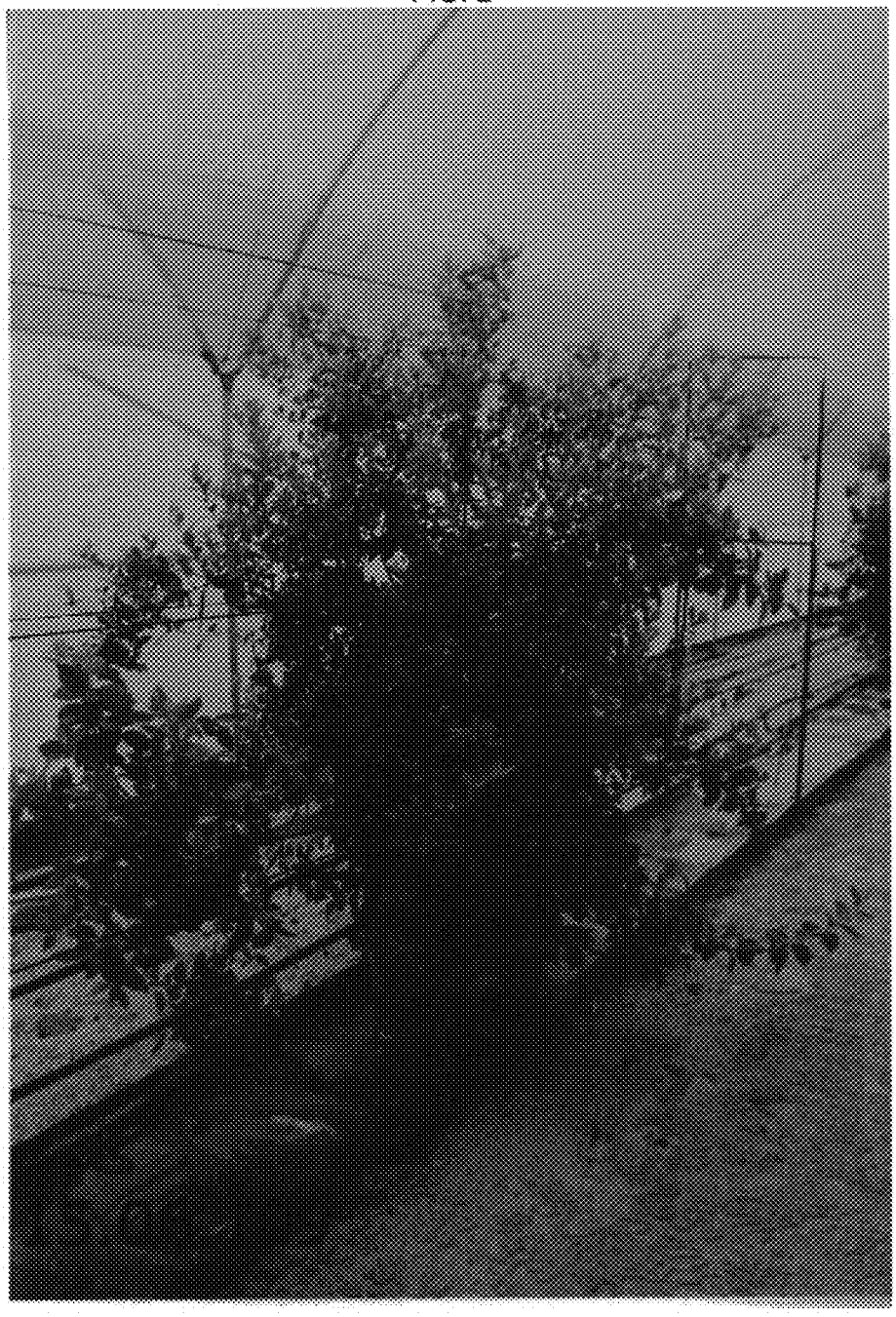
Figure 3:
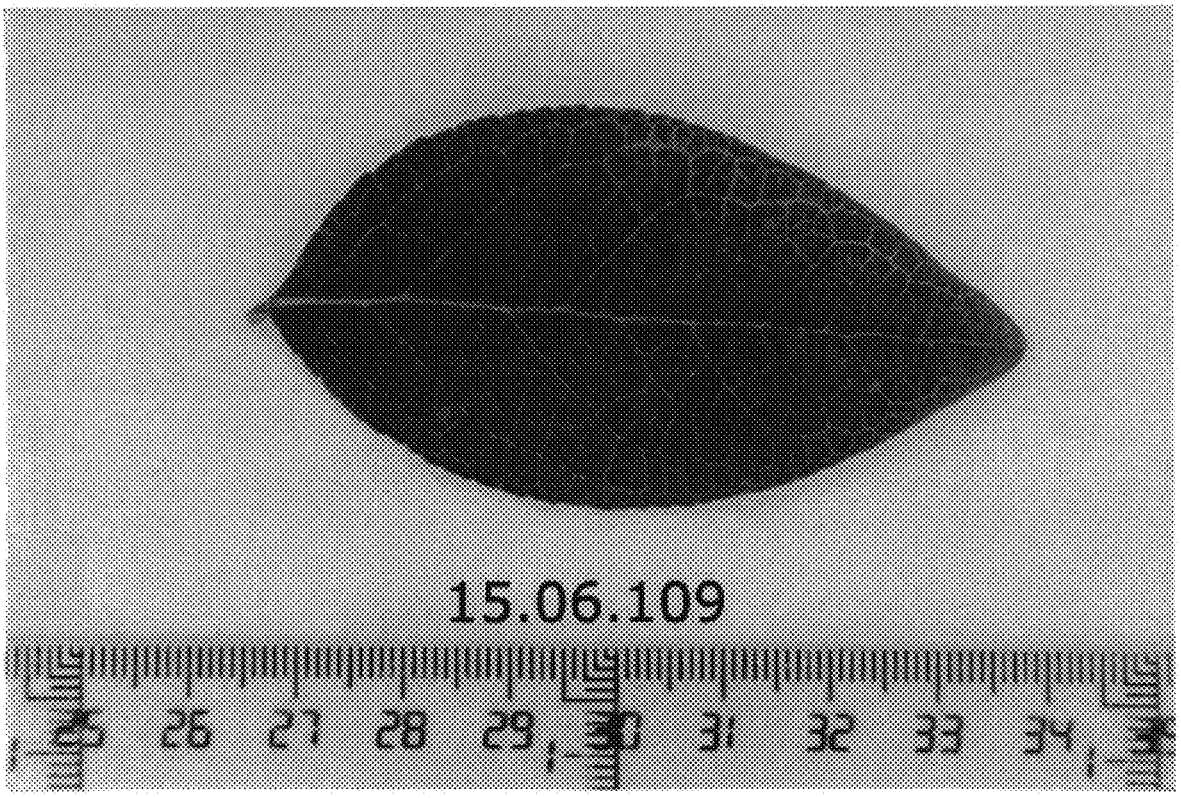
Figure 4:
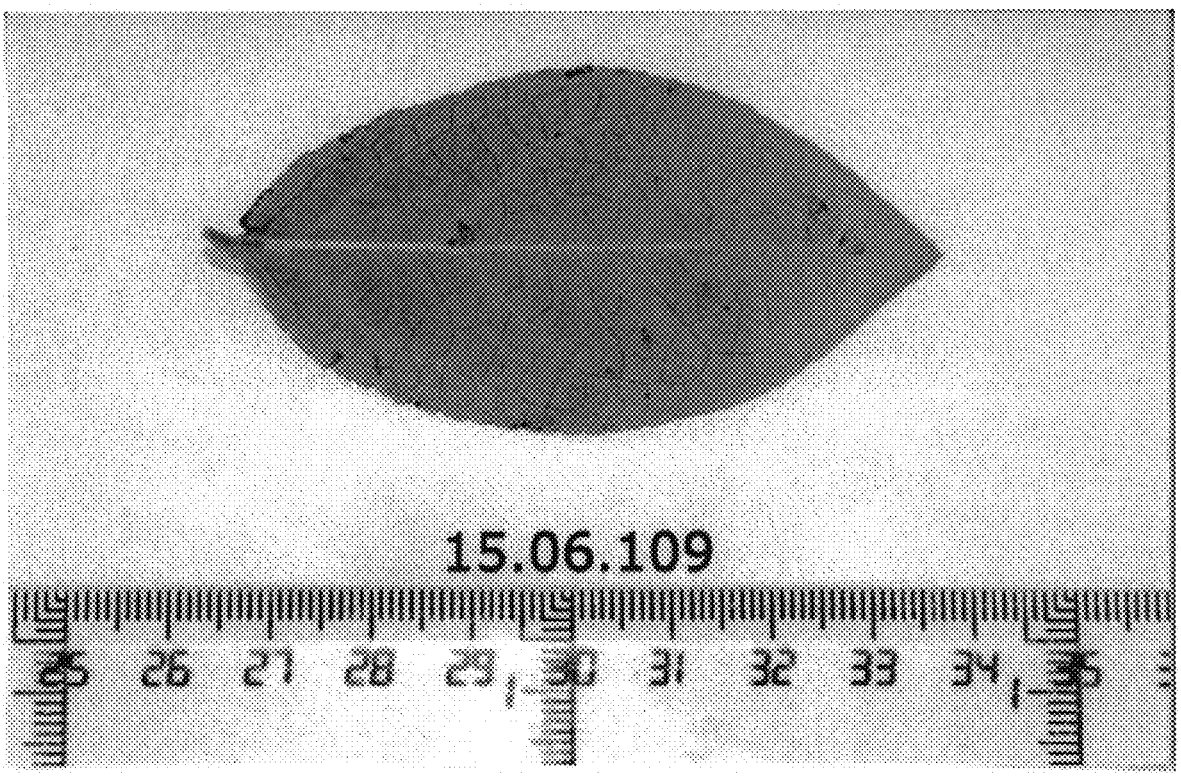
Figure 5:
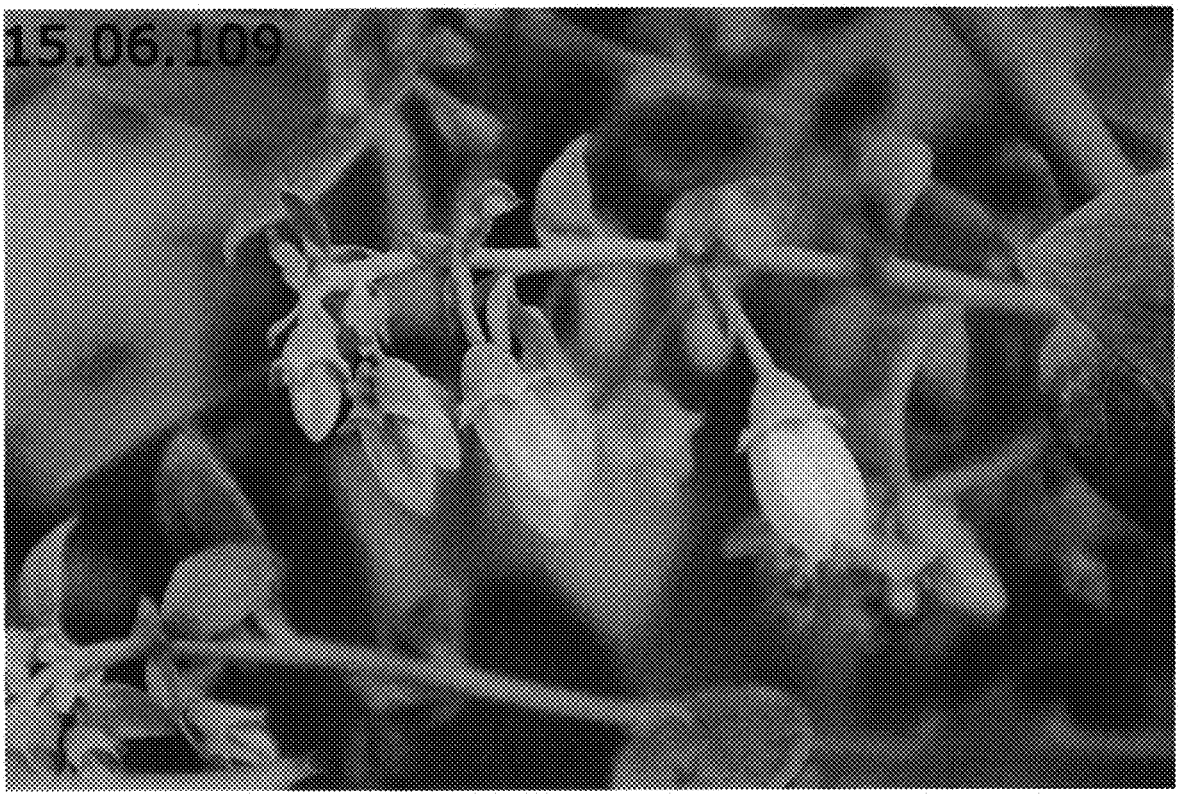
Figure 6:
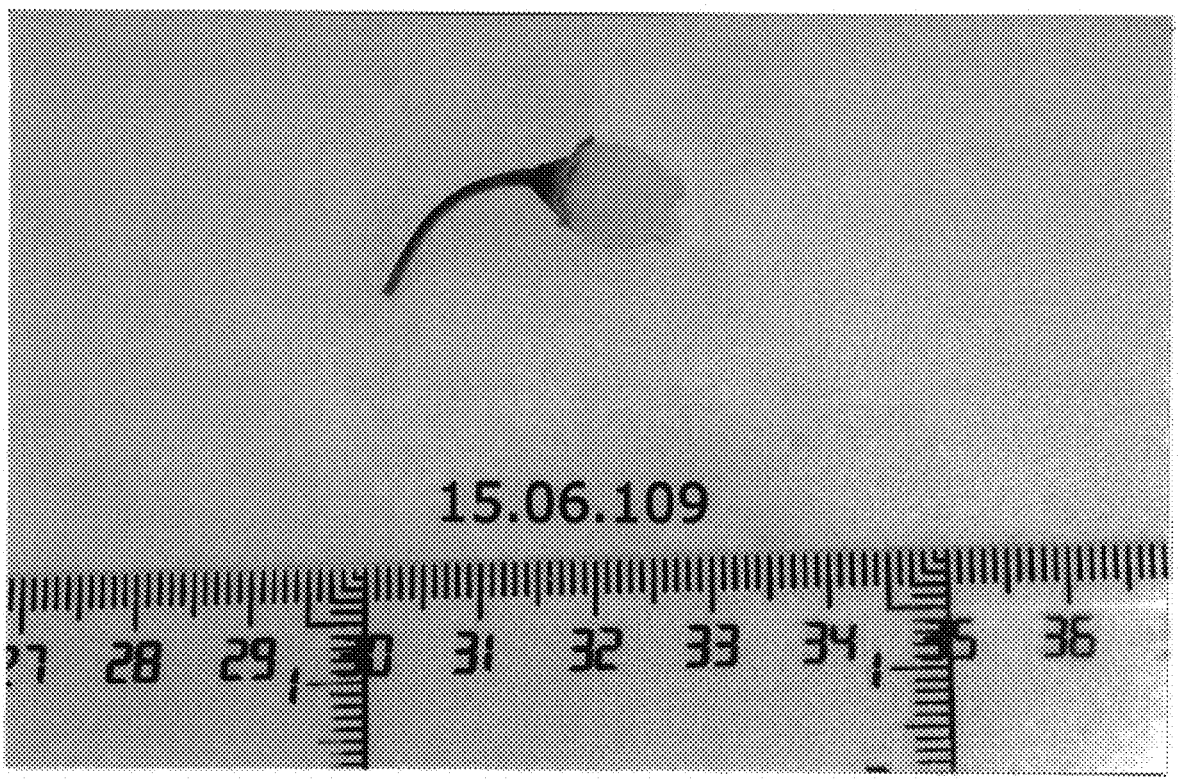
Figure 7:
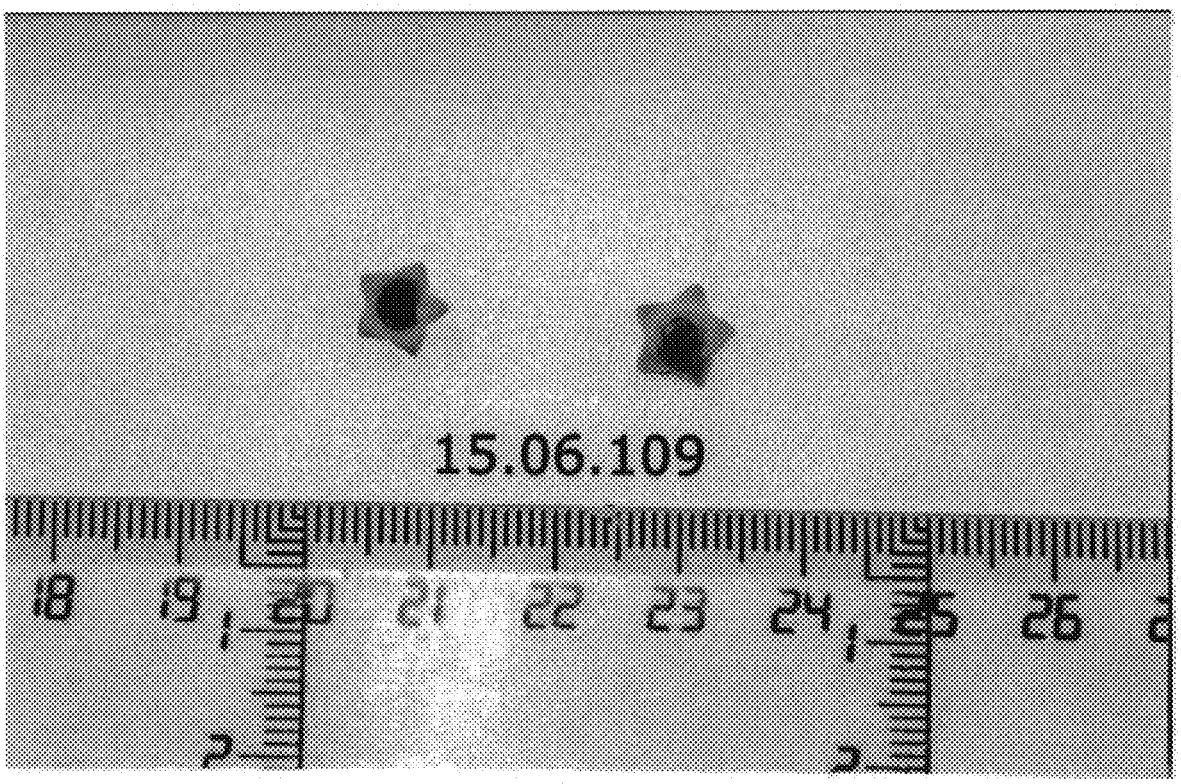
FIG. 7 shows typical sepals of the new variety (designated 15.06.109) with yellow-green color (RHS Yellow-Green group color near 144 C to 144 B).
Figure 8:
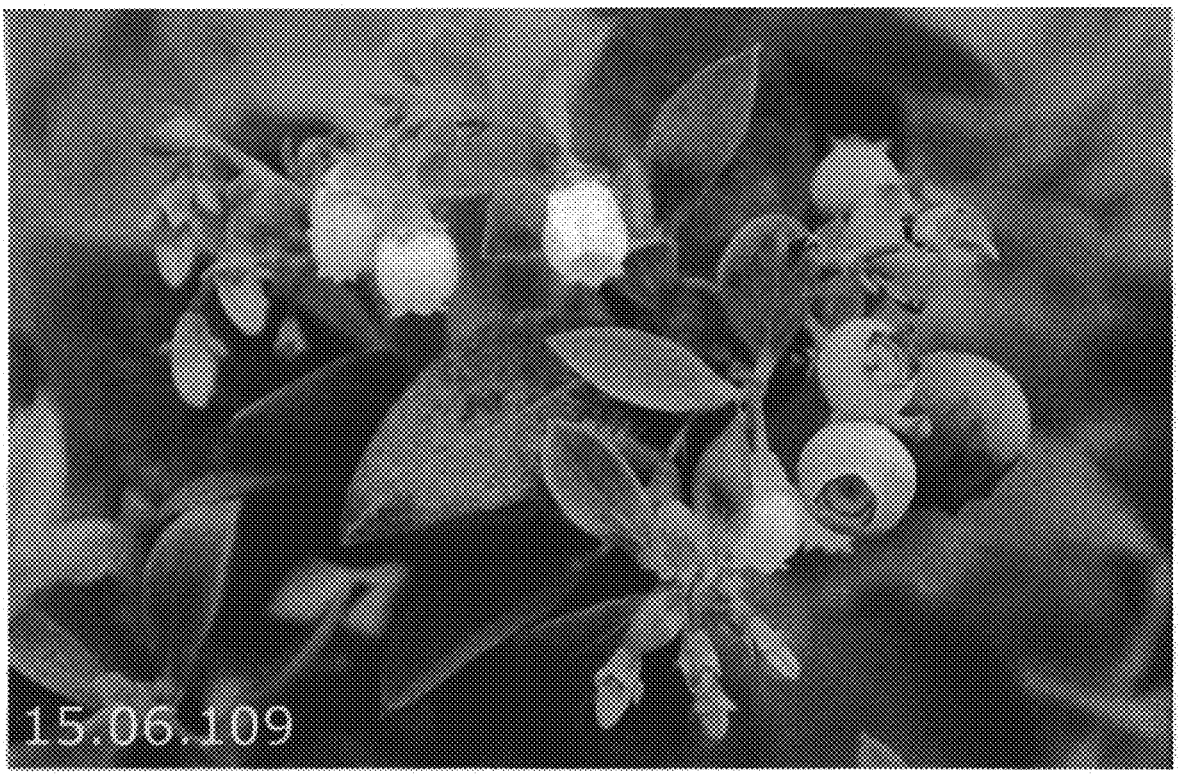
FIG. 8 shows the density of flower and fruit cluster of the new variety (designated 15.06.109).
Figure 9:
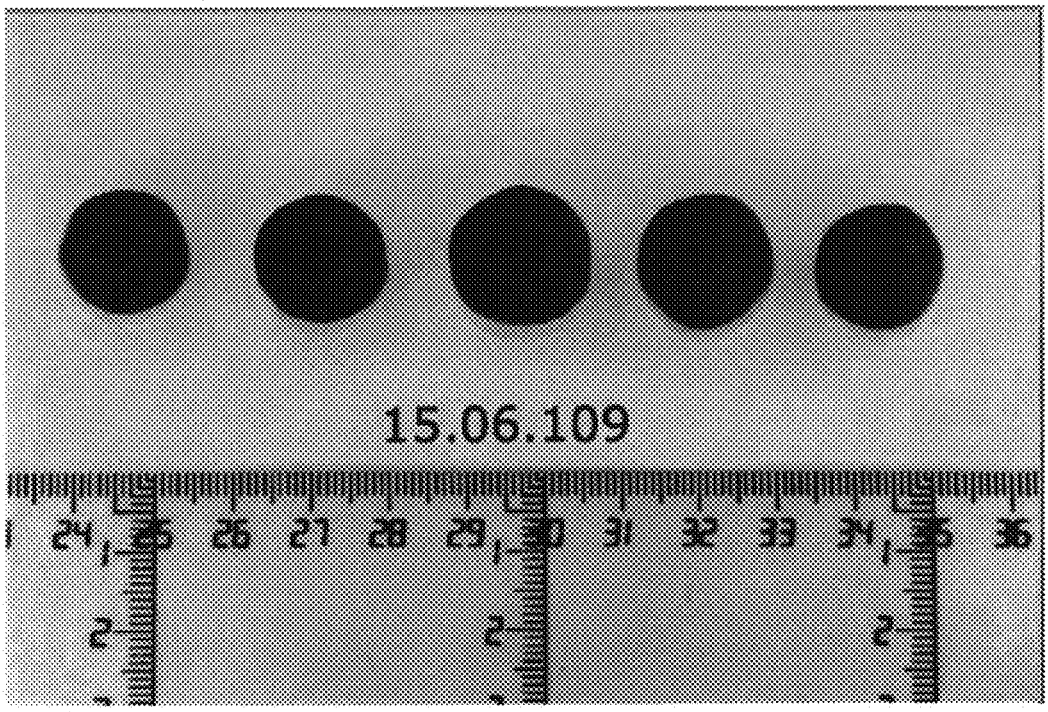
FIG. 9 and FIG. 10 show typical fruits of the new variety (designated 15.06.109) with round shape and violet-blue color with wax (RHS Violet-Blue group color near 97 C to 97 B).
Figure 10:
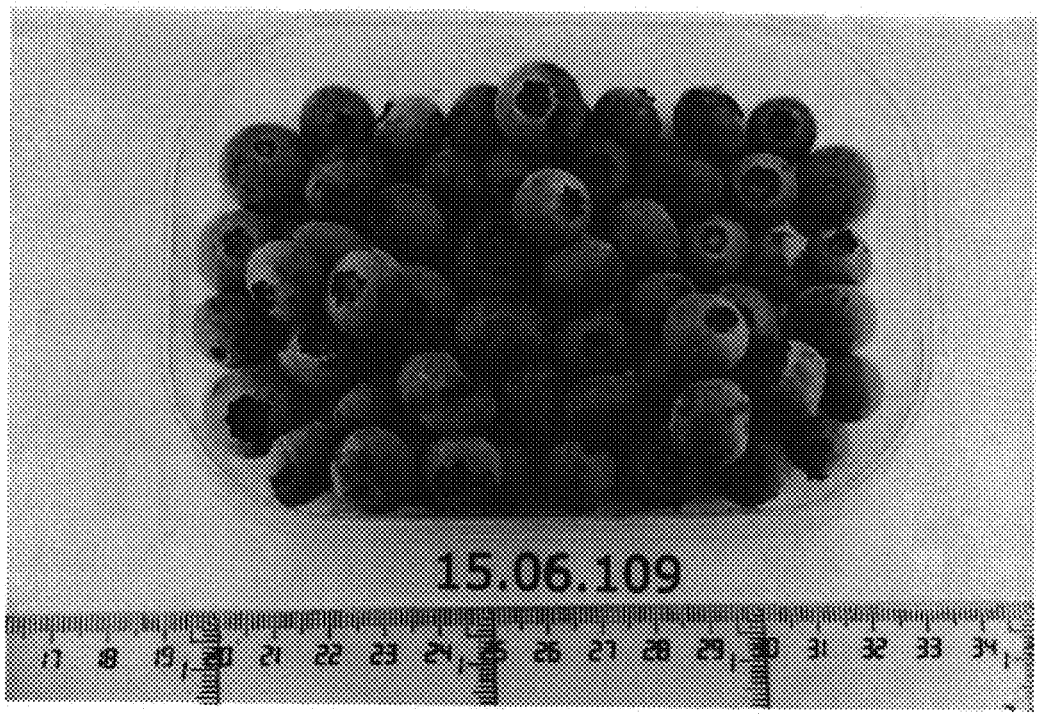
Figure 11:
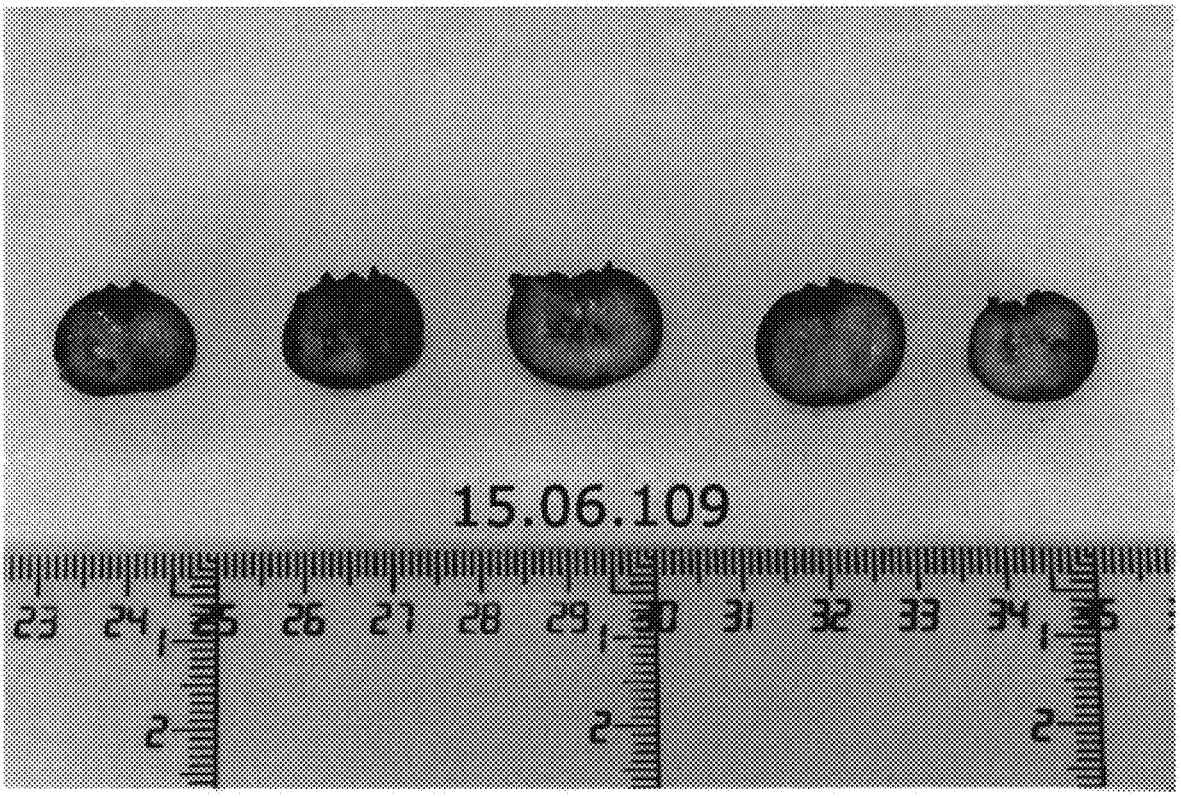
FIG. 11 shows typical sliced fruits of the new variety (designated 15.06.109) with yellow-green flesh color (RHS Yellow-Green group color near 145 D to 145 C).
Figure 12:
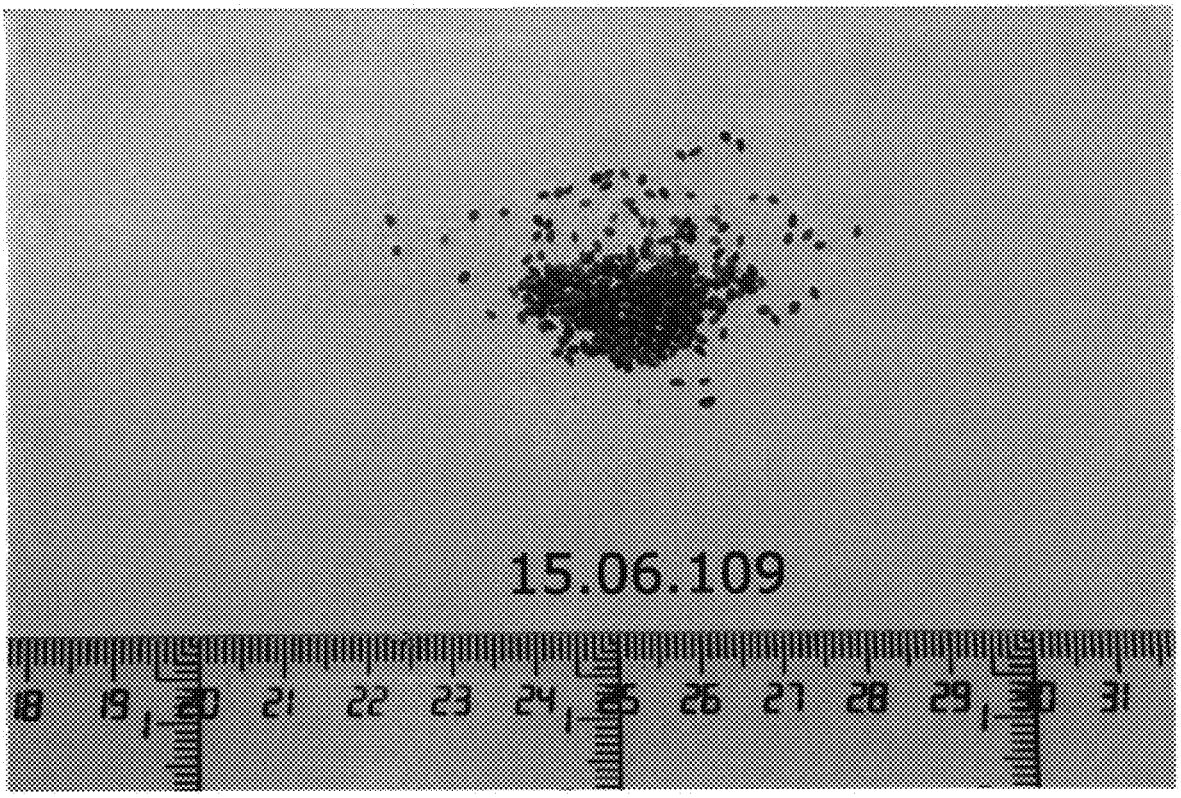
FIG. 12 shows typical seeds of the new variety (designated 15.06.109) with greyed-orange color (RHS Greyed-Orange group color near 165 B to 165 A).
Figure 13:
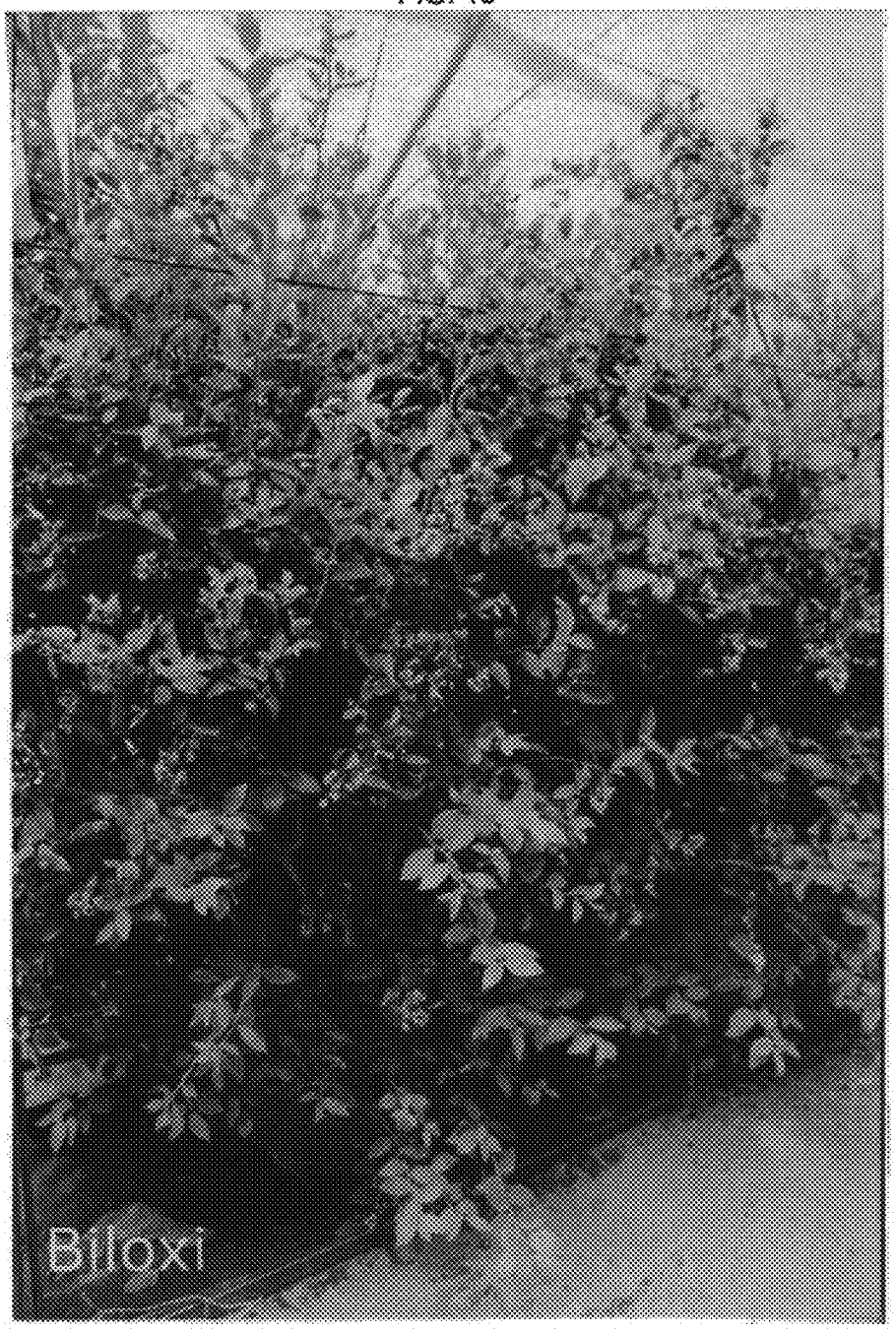
FIG. 13 shows several plants of the blueberry variety 'Biloxi' (unpatented), which exhibits a weak vigor.
Figure 14:
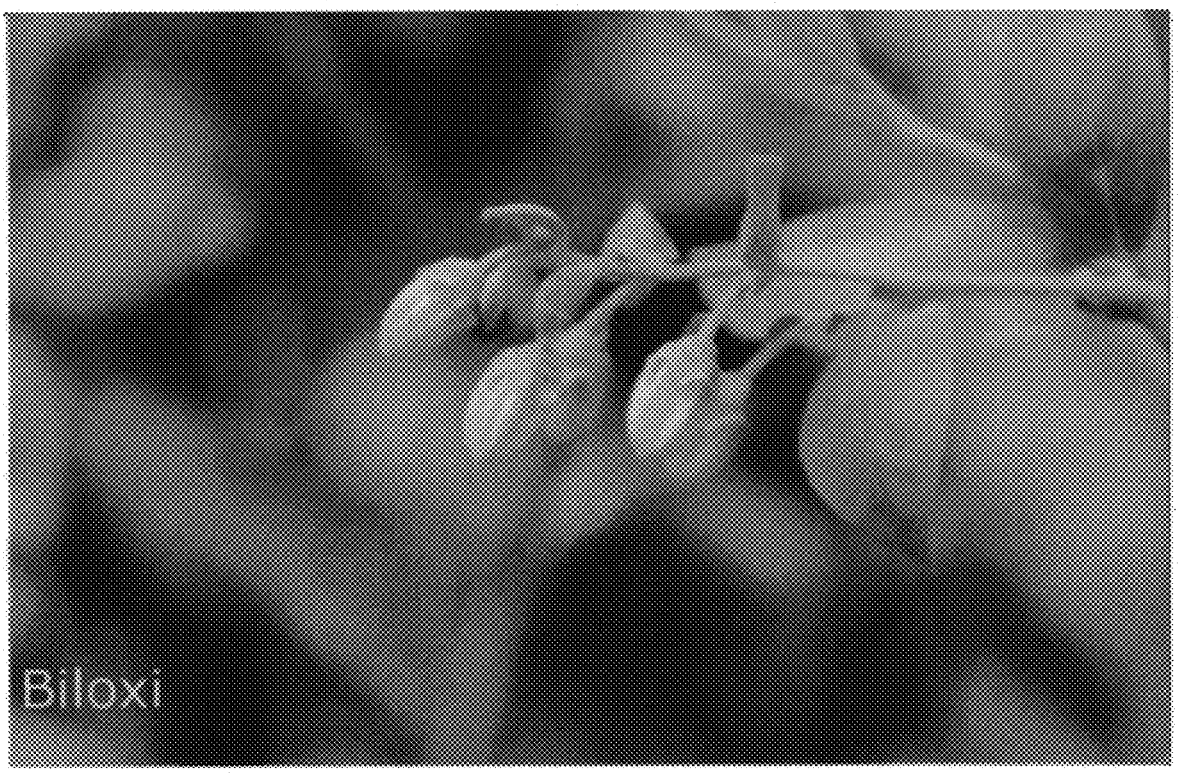
FIG. 14 shows the inflorescence of blueberry variety 'Biloxi' (unpatented) with immature flower buds which exhibits a weak anthocyanin coloration of flower bud and a short length.
Figure 15:
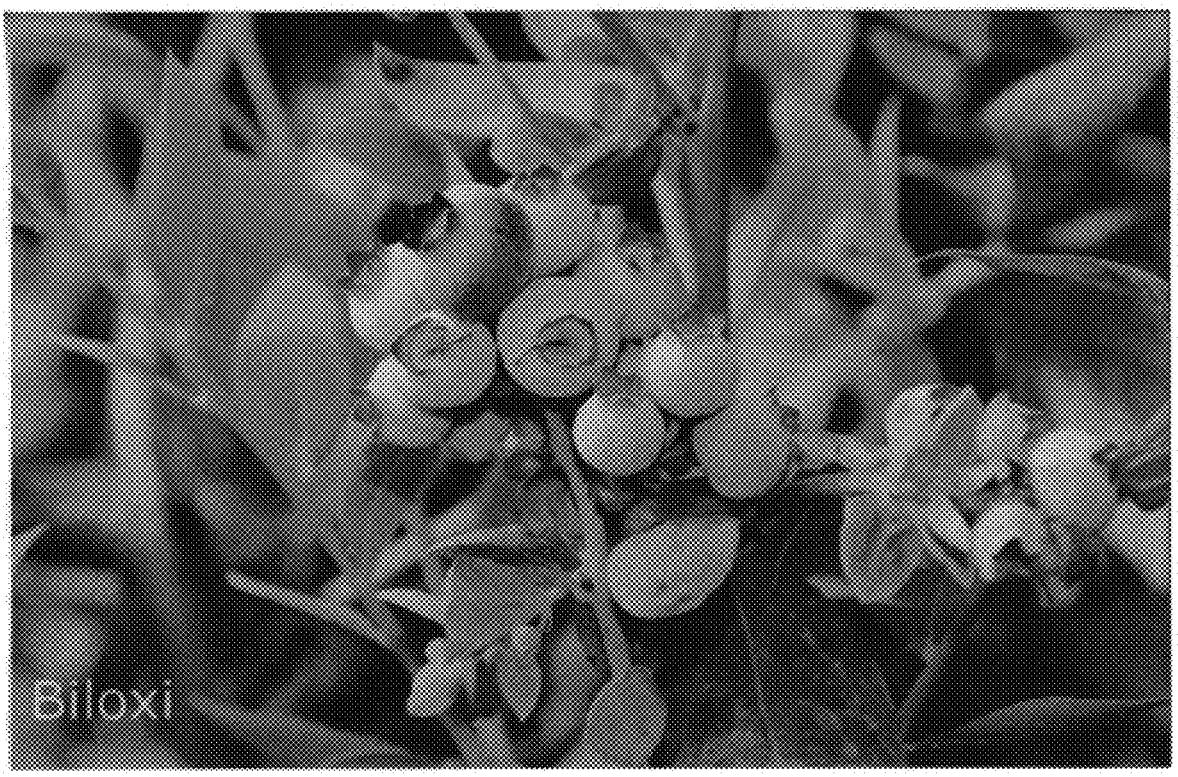
FIG. 15 shows the density of fruit cluster of 'Biloxi' (unpatented).
Figure 16:
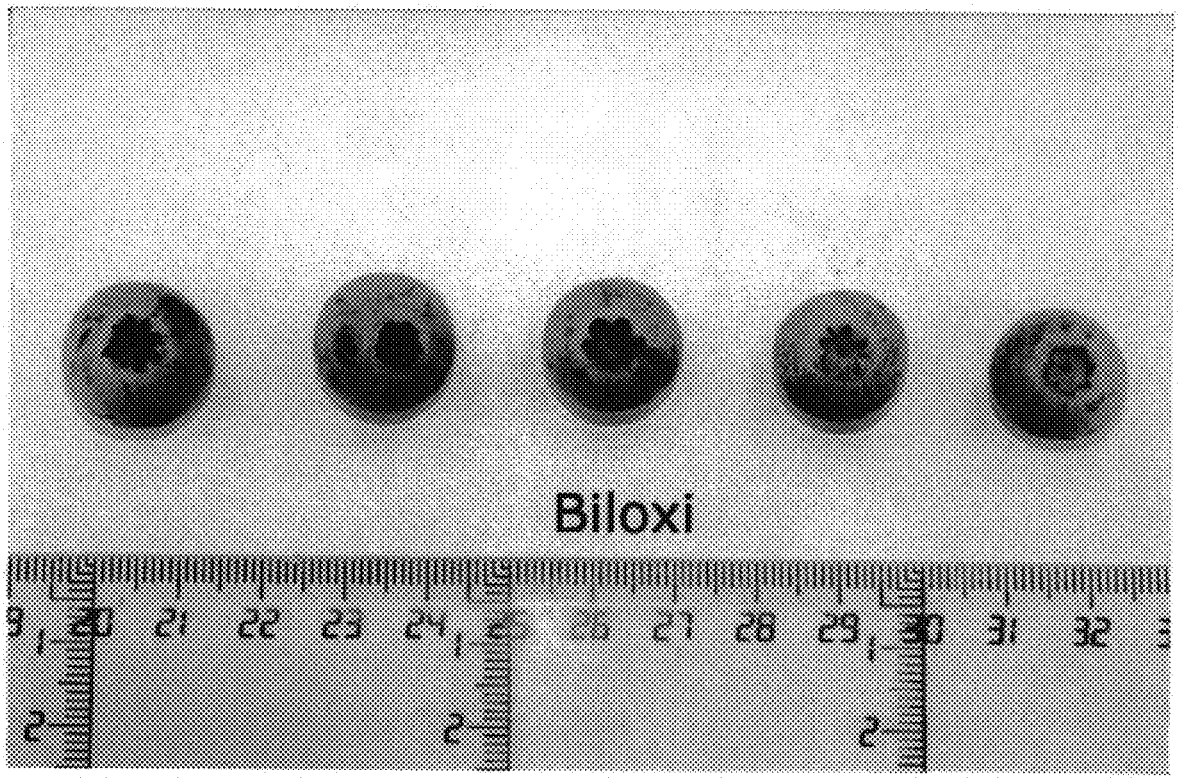
FIG. 16 shows the fruit of blueberry variety 'Biloxi' (unpatented), which exhibits an oblate shape and a sallow depth of calyx basin.
Figure 17:
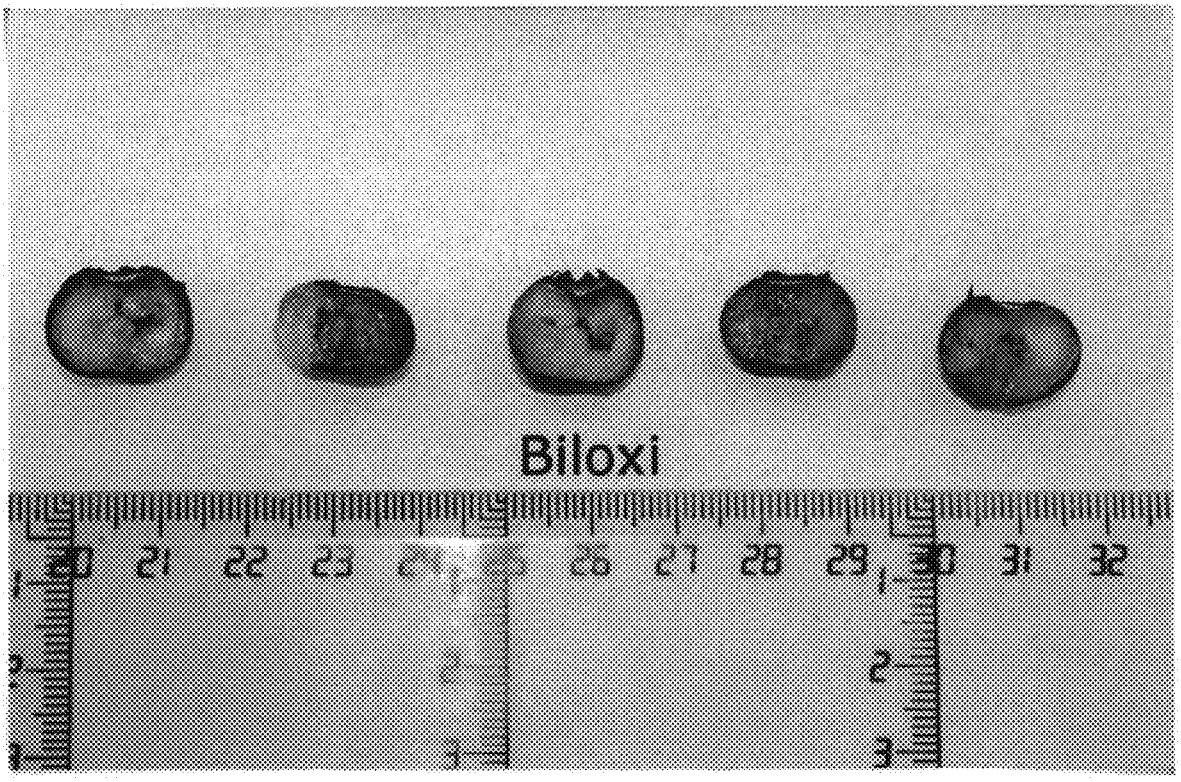
FIG. 17 shows sliced fruits of blueberry variety 'Biloxi' (unpatented), which exhibits a shallow depth of calyx basin.

The following detailed description of the new variety is based upon observations taken of plants and fruits grown "underglass", i.e. undertunnel, in the farm in Cartaya (Huelva), Spain, 7° W., 37° N., 45 feet elevation.

The following description is in accordance with UPOV terminology and the color teminology herein is in accordance with The Royal Horticultural Society Colour Chart (R.H.S.C.C.), 3rd edition published in 1995. The color descriptions and other phenotypical descriptions may deviate from the stated values and descriptions depending upon variation in environmental, seasonal, climatic and cultural conditions.

PROPAGATION

The new variety is principally propagated by softwood cuttings. Although propagation by softwood cuttings is presently preferred, other know methods of propagating blueberry plants may be used. Blueberry root and develop well after transplanting.

GENERAL

'Plablue 15122' is propagated by softwood cuttings. It is a variety with fruit production from ending January through ending May. It is a self-fertile variety. It produces large quantity of pollen throughout the seasons and pollination is good.

Production: Plants described are from high elevation nursery in Segovia, Spain, 3° 59'W., 41° 22'N., 2742 feet elevation.

Trials pursued in Cartaya (Huelva), Spain.

*Date of planting.*—14th October.

*Number of repetitions.*—2.

*Plants per repetition.*—50.

TABLE 1

Table 1 shows the accumulated production of fruit (g/plant) of the new variety 'Plablue 15122' when compared to its closest varieties 'Biloxi' and 'Star'.

| Variety | February 27 | March 31 | April 30 | June 22 |
|---|---|---|---|---|
| Plablue 15122 | 978.67 | 1728.67 | 2755.00 | 4113.20 |
| Biloxi | 191.67 | 477.33 | 905.33 | 2850.00 |
| Star | 0.00 | 757.67 | 1781.73. | 1803.10 |

TABLE 2

Table 2 shows the weight (g/fruit) at three dates of the new variety 'Plablue 15122' when compared to its closest varieties 'Biloxi' and 'Star'.

| Variety | March 31 | April 30 | June 22 |
|---|---|---|---|
| Plablue 15122 | 18.00 | 16.00 | 15.00 |
| Biloxi | 16.00 | 14.00 | 14.00 |
| Star | 18.00 | 18.00 | 17.00 |

**Weight is shown as the average weight per fruit

DETAILED DESCRIPTION OF THE NEW VARIETY

The following additional information is provided to further describe the new variety.

*Variety.*—'Plablue 15122'. Breeder Ref. 15.06.109.

*Latin name.*—*Vaccinium corymbosum* L.

*Common name.*—Southern highbush blueberry. Plants are growing in containers of 45 liters of capacity.

Plant:

*Habit.*—Semi upright.

*Vigor.*—Medium.

*Height of plant.*—About 1.80 to 1.90 m.

*Canopy diameter.*—About 1.20 to 1.30 m.

*Twigginess.*—Medium.

*Suckering.*—High.

*Evergreenness.*—Evergreen.

*Chilling requirement.*—Approximately 100-200 hour at temperatures at or below 7° C.

*Cold hardiness.*—Has not been grown in all environments including harsh winter environments. Cold tolerance is expected to be low.

Trunk and branches:

*Surface texture new wood.*—Smooth.

*Surface texture* 1 *year wood.*—Smooth.

*Surface texture* 2 *years and older wood.*—Rough.

*Diameter new wood.*—About 3.0 to 3.5 mm.

*Diameter* 1 *year wood.*—About 7.5 to 8.5 mm.

*Diameter* 2 *years old wood.*—About 14.5 to 15.5 mm.

*Color.*—New wood about green color (RHS Green group color near 143 D to 143 C) transitioning to about greyed-orange color (RHS Greyed-Orange group color near 177 C to 177 A) in about 2 year old wood.

Leaf:

*Internode length.*—About 22.50 to 24.0 mm.

*Leaf arrangement.*—Alternate simple.

*Length.*—About 6.8 to 7.2 cm.

*Width.*—About 3.8 to 4.3 cm.

*Leaf shape.*—Elliptic.

*Shape of tip.*—Acute.

*Shape of base.*—Acute.

*Shape of margin.*—Serrate.

*Venation pattern.*—Reticulate.

*Mature leaf color upperside.*—RHS Yellow-Green group color near 147 B to 147 A.

*Mature leaf color underside.*—RHS Yellow-Green group color near 148 D to 148 C.

*Pubescence upper leaf surface.*—Absent.

*Pubescence under leaf surface.*—Present.

*Pubescence leaf margin.*—Present.

*Precocity.*—New vegetative growth before flowering.

Petiole:

*Length.*—About 2.5 to 3.0 mm.

*Width* (*diameter*).—About 1.5 to 2.0 mm.

*Texture.*—Smooth.

*Color.*—RHS Yellow-Green group color near 145 C to 145 B.

Flower:

*Flower arrangement.*—Compound raceme. Clusters at the end of branches.

*Flower shape.*—Urceolate.

*Flowers per cluster.*—About 7 to 8.

*Flower fragrance.*—Pleasant.

*Immature flower color*.—RHS Red group color near 55 D to 55 B.

Corolla:

*Length*.—About 8.5 to 9.0 mm.

*Diameter*.—About 5.0 to 6.0 mm.

*Aperture width*.—About 3.0 to 4.0 mm.

*Color*.—RHS White group color near 155 B to 155 A.

*Texture*.—Smooth.

Peduncle:

*Length*.—About 14.5 to 15.5 mm.

*Color*.—RHS Yellow-Green group color near 144 C to 144 B.

Pedicel:

*Length*.—About 12.5 to 13.0 mm.

*Color*.—RHS Yellow-Green group color near 144 C to 144 B.

*Calyx (with sepals) diameter*.—About 7.5 to 8.5 mm.

*Calyx texture*.—Smooth.

*Color center of calyx*.—RHS Green group color near 143 B to 143 A.

*Color sepals*.—RHS Yellow-Green group color near 144 C to 144 B.

*Attitude of sepals*.—Erect.

*Type of sepals*.—Reflexed.

Stamen:

*Length*.—About 5.5 to 6.0 mm.

*Number per flower*.—About 10 to 11.

*Filament color*.—RHS yellow-green group color near 145 D to 145 C.

Style:

*Length*.—About 8.0 to 9.5 mm.

*Color*.—RHS Yellow-Green group color near 145 C to 145 B.

Pistil:

*Length*.—About 9.5 to 10.0 mm.

*Ovary color*.—RHS Yellow-Green group color near 145 D to 145 C.

Anther:

*Length*.—About 2.9 to 3.2 mm.

*Number*.—About 10 to 13.

*Color*.—RHS Greyed-Orange group color near 166 C to 166 B.

Pollen:

*Abundance*.—High.

*Color*.—RHS Yellow-Orange group color near 20 C to 20 B.

*Self-compatibility*.—The cultivar has demonstrated a high degree of self-compatibility.

Fruit:

*Fruiting type*.—On one-year-old and current season's shoots.

*Calyx aperture*.—About 7.0 to 8.0 mm.

*Calyx lobes*.—About 5 to 6 lobes.

*Calyx depth*.—About 1.5 to 2.0 mm.

*Pedicel length*.—About 10.5 to 11.0 mm.

*Pedicel surface texture*.—Smooth.

*Peduncle length*.—About 13.5 to 14.0 mm.

*Peduncle surface texture*.—Smooth.

*Berries per cluster*.—About 7 to 8.

*Berry detachment*.—Easy.

*Weight*.—About 15 to 18 grs.

*Height*.—About 13.0 to 14.0 mm.

*Width*.—About 17.0 to 18.5 mm.

*Shape*.—Round.

*Color with wax*.—RHS Violet-Blue group color near 97 C to 97 B.

*Color with wax removed*.—RHS Black group color near 202 A.

*Persistent wax*.—High

*Surface wax abundance*.—Moderate.

*Flesh color*.—RHS Yellow-Green group color near 145 D to 145 C.

*Pedicel scar*.—About 1.1 to 1.6 mm.

*Firmness*.—0.8 Kg. Firmness: It is the fruit's resistance to penetration measured in Kilograms (Kg). The measure given has been obtained by the penetrometer ROZE Mod. Arbelette, with a 20 $mm^2$ section head.

*Texture of flesh*.—Crisp.

Seed:

*Color*.—RHS Greyed-Orange group color near 165 B to 165 A.

*Length*.—About 1.0 to 2.0 mm.

*Width*.—About 0.90 to 1.0 mm.

*Weight*.—About 0.3 to 0.4 mg.

*Seeds per berry*.—About 16 to 18.

General: The growing period in Huelva, Spain, where the observations on primocane production were made, is between about November 20 and June 22 of the following year. 'Plablue 15122' is a blueberry variety that benefits from induction to flowering by chilling, usually a few hours (approximately 100-200 hours) are sufficient, preferably at temperatures of 7° C. or less. Normally, the minimum number of hours is accumulated in the field during several days. 'Plablue 15122' is a variety with consistent fruit production beginning at the end of January and ending at the end of May. After planting as aforesaid, plants are grown in containers under tunnel. Water and fertilizer were applied through drip irrigation.

Date of planting: About October 15 in the farm in Cartaya (Huelva), Spain, about 7° W, 37° N, 45 feet elevation. Time of flowering data: 10% flowering about October 28. First mature fruits are about January 29 (15-20 g/plant), with a maximum production at the end of April.

Storage qualities: 'Plablue 15122' fruit maintains their quality characteristics when keeping them in a frigo chamber at temperatures of about 2° C. during 30 days. The fruit's color remains substantially the same. Shelf life of 'Plablue 15122' is good.

Use/market: The berries of 'Plablue 15122' are suitable for consumption as fresh fruit. Also, they are amenable to processing.

Disease resistance: No particular sensitivity to any disease or pest has been observed for 'Plablue 15122'.

I claim:

1. A new and distinct blueberry plant of the variety substantially as shown and described.

* * * * *